US00PP08951P

United States Patent [19]

Wandell

[11] Patent Number: Plant 8,951

[45] Date of Patent: Oct. 18, 1994

[54] SYRINGA PEKINENSIS

[76] Inventor: Willet N. Wandell, R.R. 1, Box 286, Oquawka, Ill. 61469

[21] Appl. No.: 112,078

[22] Filed: Aug. 26, 1993

[51] Int. Cl.[5] ..... A01H 5/00

[52] U.S. Cl. ..... Plt./66

[58] Field of Search ..... Plt. 51.1, 66

*Primary Examiner*—James R. Feyrer

[57] ABSTRACT

This is a variety of *Syringa pekinensis* and has been reproduced asexually from a tree found growing at Milwaukee, Wisconsin with the characteristics of an upright growth habit of 12 feet wide and 18 feet tall without the benefit of cultural pruning and trimming. Propagated by me asexually it produced straight-growing progeny with a strong central leader; a tree crown producing an abundance of fine textured deep green leaves and large cream colored flower trusses annually. The bark is a lustrous reddish-brown with many very horizontal lenticels. Progeny produced show rapid and sustained growth.

5 Drawing Sheets

BACKGROUND OF INVENTION

This speciment of *Syringa pekinenesis* was found growing in a cultivated area of a suburb of Milwaukee, Wis. in clay soil on a rolling terrain area. This tree, growing singularly and away from other trees, showed a strong upright growth habit, a good, stout limb scaffold and full fine-textural crown. I produced 165 progency by chip budding from the parent tree in my nursery at Urbana, Ill.; as they grew all exhibited the above characteristics of the present tree. In addition, all bloomed abundantly the second year from budding and exhibit spontaneity of bloom, which in later years reoccurred annually. I was also attracted to the tree by its abundance of lustrous dark-green leaves during the growing season, as well as its attractive bark.

SUMMARY OF INVENTION

A new and distinct cultivar of *Syringa pekinenesis* characterized by an upright growth habit, reliable blooming period of fragrant bloom trusses; thick shiny leaves borne in abundance and lustrous deep reddish-brown bark with pronounced lenticels.

DESCRIPTION OF THE NEW PLANT

Figure 1:
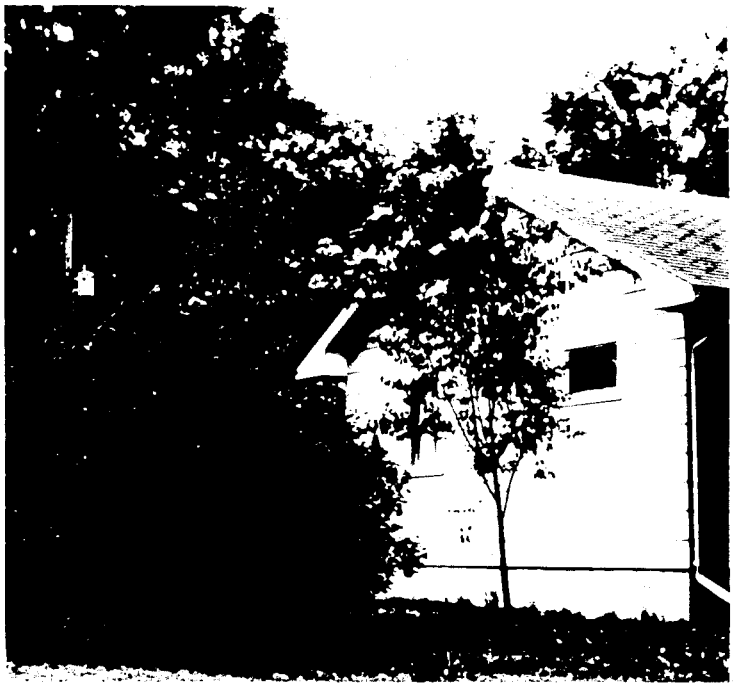
FIG. 1: Shows the upright form of 'Summer Charm' and the manner in which bloom trusses are borne. Density of tree, when in full leaf, shows a heavy canopy of small leaves which, when viewed laterally shows no intrusion of the background.
Figure 2:
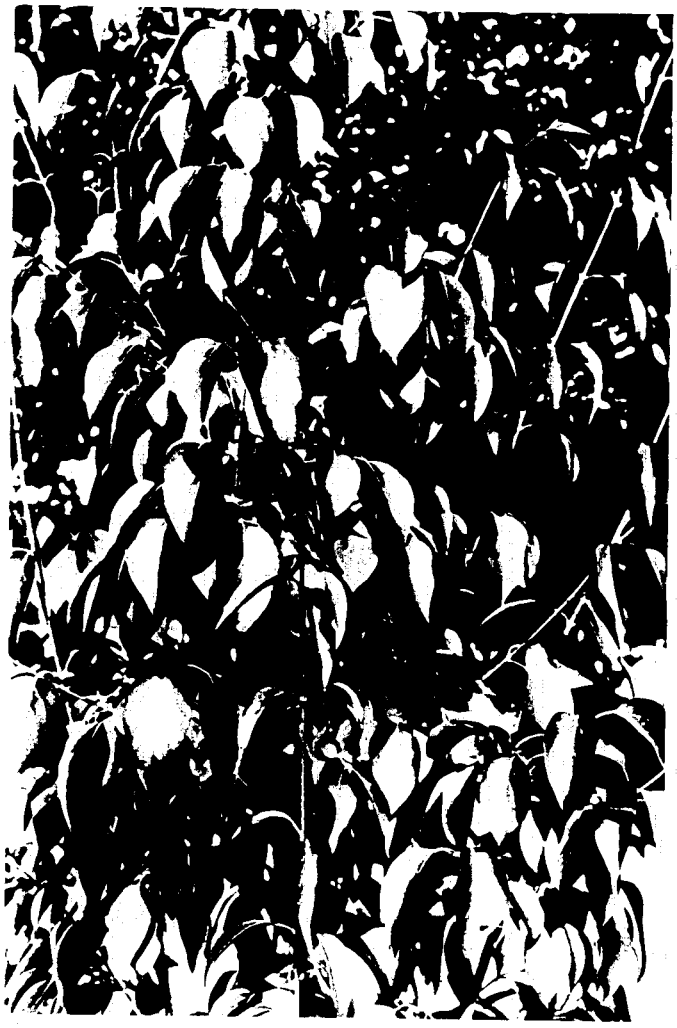
FIG. 2: Shows the abundance of leaves carried by the tree crown and the green lustre during the growing season. The color of the leaves are a deeper green and more lustrous than the species and also borne in greater abundance on a disciplined narrow upright crown. Twigs of the new or current years growth are a bright green (R.H.S. group 143C) maturing into a color best described as R.H.S. greyed-purple group 184C.
Figure 3:
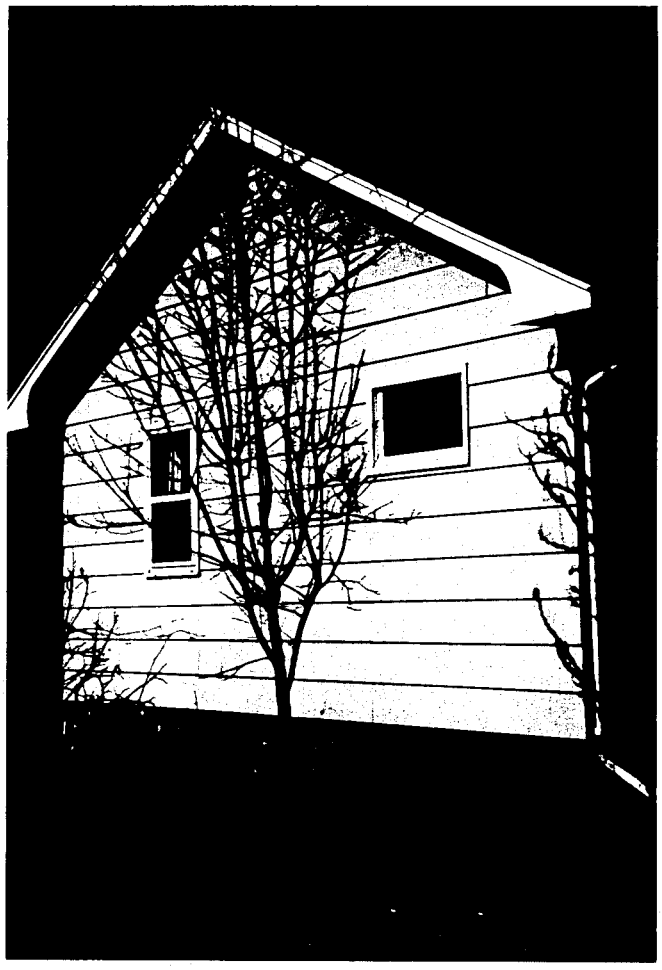
FIG. 3: Shows the upright trunk structure of 'Summer Charm' whose shape is spontaneous and is maintained without trimming and pruning.
Figure 4:
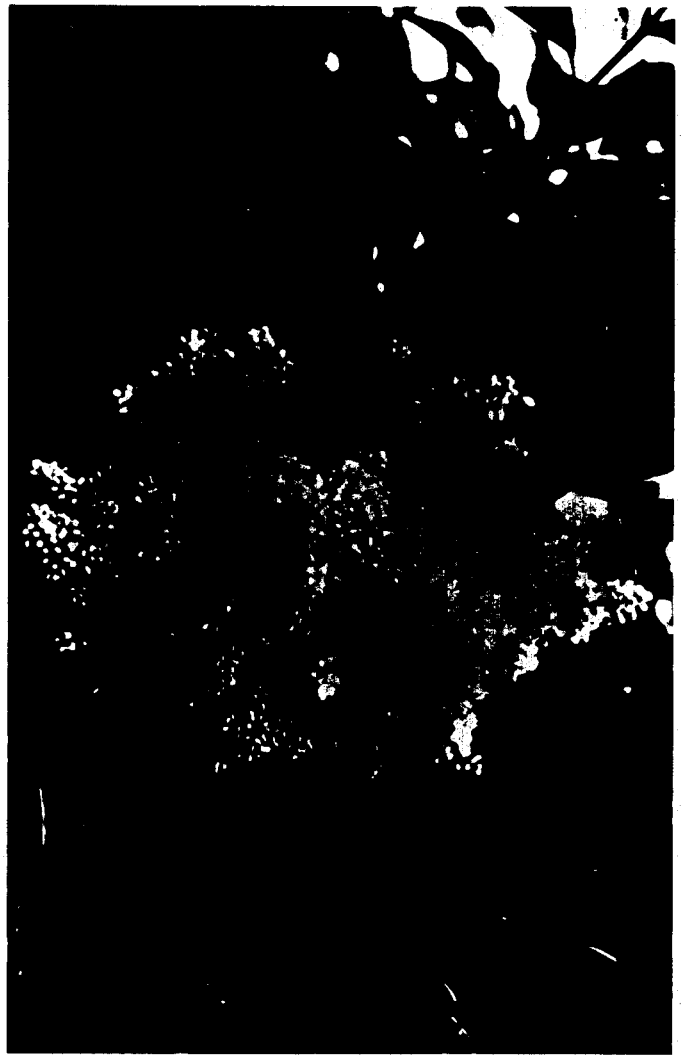
FIG. 4: Shows the ample size of bloom trusses and lustre and deep green color of leaves.
Figure 5:
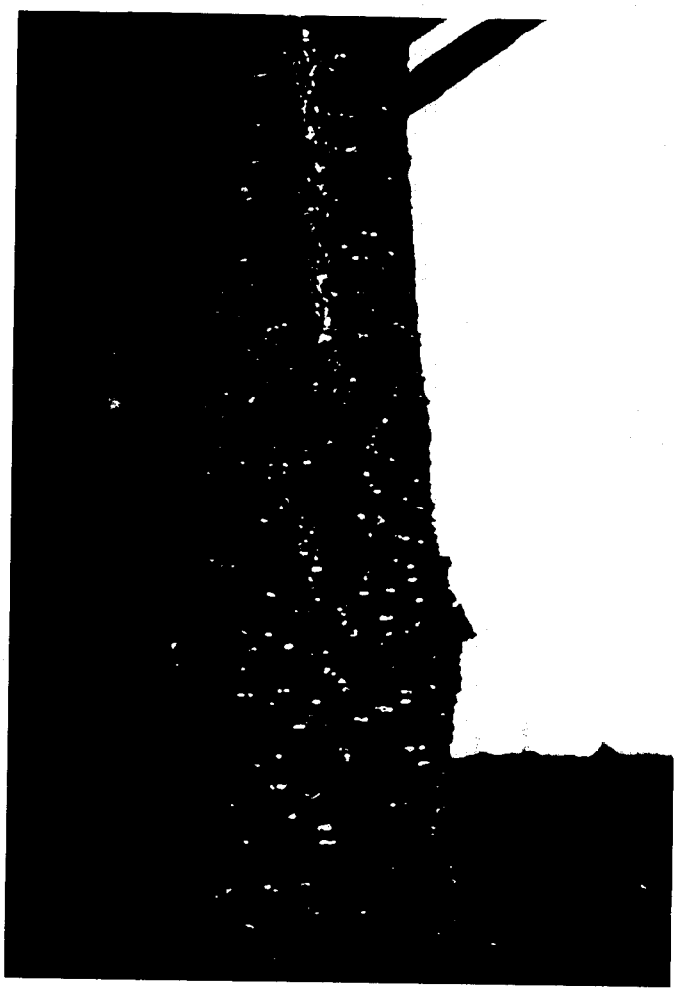
FIG. 5: Shows the sheen of the dark attractive bark and rich endowment of horizontal lenticels.

The following is a detailed description of my new variety of *Syringe pekinensis* lilac tree with color designations according to the R.H.S. Colour Chart published by The Royal Horticultural Society of London, England and the stated observations having been made on trees growing in Oquawka, Ill. by the applicant and found to distinguish from the species. The colors of the plant parts of this tree have been observed to not differ from those of the species in general and are not seen to distinguish the tree. Accordingly, only verbal, general color designations are presented below.

Origin: This tree was discovered in an open planting of collected trees in East Central Wisconsin.

Classification: *Syringa pekinensis.*

Parentage: *Syringa pekinensis* by assumption.

Form: A small upright tree maturing 12 feet wide and 18 feet tall.

Habit: Small tree to 18 feet tall, with a single main stem and leader instead of the multi-stem and leader habit typical of the species; crown narrowly pyramidal in shape; branches strongly ascending.

Twigs: Straight, orange-brown, glabrous, with numerous round lenticels.

Buds: Opposite, sessile, solitary, subconical 2 mm long, with 4 pairs of scales, the terminal bud often lacking; leaf scars opposite, raised crescent-shaped, with one bundle trace.

Bark: Smooth, orange or reddish-brown, with very elongate horizontal lenticles.

Leaves: Deciduous, opposite, simple, pinnately veined, hanging downwards, leaf blades narrowly ovate, 4–8 cm long and 2.2–3.5 cm. wide, the margins entire and minutely ciliolate, the apices broadly acuminate, the basis rounded, glabrous above and below, lustrous green above, paler below; petioles 1.5–2.5 cm long; fall color deep yellow; smaller than plants typical of the species and produced in greater quantity, resulting in a finer overall texture.

Inflorescences: Large, many-branched panicles, the main branches up to 15 cm long, extremely showy, produced at the tips of growth of the current year after the leaves have emerged; flowering heavily each year, instead of every 2 or 3 years, as is typical of the species. Fragrance is persistant and although pleasant can be over-powering in closely confined areas-usually not a problem in modern living and dwelling areas.

Flowers: Perfect, creamy-white (R.H.S. 11D); calyx tube faintly 4-lobed, 1.5 mm long; corolla of 4 petals connate at the base, 5–6 mm long, deeply 4-lobed, the lobes recurved; stamens 2, exserted, attached at the base of the corolla tube, the filaments 5–7 mm long; carpels 2, connate, the ovary superior, the style 1 mm long, the stigma solitary, narrowly obovoid 0.5 mm long. The color of the pollen shed is initially the color of R.H.S. yellow-orange group 18A but soon shows a majority of the individual pollen grains darkening to R.H.S. greyed-orange group 165B.

Fruit: Capsules, 1.01.6 cm long, 0.3–0.4 mm wide, laterally flattened, with numerous lenticels, dehiscing by 2 valves to release 1 to 2 seeds.

I claim:

1. A new and distinctive variety of *Syringa pekinensis* named 'Summer Charm' as shown and described herein that differs from all other varieties by the unique combination of: (1) large panicles of creamy-white flowers produced annually and not intermittently; (2) narrow, upright tree habit; (3) outstandingly thick glossy, fine-textured foliage resulting from the production of an abundance of leaves borne; (4) attractive lustrous dark-brown bark with an abundance of light-colored and persistant lenticels.

* * * * *